United States Patent
Gilbert et al.

(10) Patent No.: US 7,381,201 B2
(45) Date of Patent: Jun. 3, 2008

(54) REUSABLE, SPRING DRIVEN AUTOINJECTOR

(75) Inventors: Scott Gilbert, Menlo Park, CA (US); Pedro de la Sema, San Jose, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/603,513

(22) Filed: Jun. 24, 2003

(65) Prior Publication Data

US 2004/0019326 A1 Jan. 29, 2004

Related U.S. Application Data

(60) Provisional application No. 60/391,322, filed on Jun. 24, 2002.

(51) Int. Cl.
*A61M 5/00* (2006.01)

(52) U.S. Cl. .................................................. 604/181

(58) Field of Classification Search ............... 604/209, 604/117, 196, 187, 232, 134, 208, 211, 192, 604/218, 220, 224, 228, 136, 138, 156, 157, 604/181
See application file for complete search history.

(56) References Cited

U.S. PATENT DOCUMENTS

| | | |
|---|---|---|
| 3,797,489 A | 3/1974 | Sarnoff |
| 4,518,384 A | 5/1985 | Tarello et al. |
| 4,678,461 A | 7/1987 | Mesa |
| 4,894,054 A | 1/1990 | Miskinyar |
| 5,092,842 A * | 3/1992 | Bechtold et al. ............ 604/135 |
| 5,092,843 A | 3/1992 | Monroe et al. |
| 5,102,393 A | 4/1992 | Sarnoff et al. |
| 5,104,380 A * | 4/1992 | Holman et al. ............. 604/117 |
| 5,155,965 A | 10/1992 | Tabei et al. |
| 5,236,424 A * | 8/1993 | Imran ......................... 604/523 |
| 5,300,030 A | 4/1994 | Crossman et al. |
| 5,354,286 A | 10/1994 | Mesa et al. |
| 5,358,489 A * | 10/1994 | Wyrick ....................... 604/136 |
| 5,527,287 A | 6/1996 | Miskinyar |
| 5,567,160 A | 10/1996 | Massino |
| 5,665,071 A | 9/1997 | Wyrick |

(Continued)

FOREIGN PATENT DOCUMENTS

EP 0 982 518 A 3/2000

(Continued)

OTHER PUBLICATIONS

Hodgson, Darel E. et al., "Shape Memory Alloys".

(Continued)

*Primary Examiner*—Manuel Mendez
(74) *Attorney, Agent, or Firm*—Angela N. Nwaneri; Adenike A. Adebiyi; Lois Gianneschi

(57) ABSTRACT

The present invention provides a reusable spring driven autoinjector. The drive mechanism of the autoinjector of the present invention includes one or more drive springs formed of a shape memory alloy. Therefore, by alternating the shape memory alloy forming the one or more drive springs between austenite phase before an injection and a martensite phase after injection, the reusable autoinjector of the present invention is capable of providing an injection force that is higher than the compressive force required to cock the drive mechanism in preparation for a subsequent injection operation.

15 Claims, 2 Drawing Sheets

U.S. PATENT DOCUMENTS

| | | | |
|---|---|---|---|
| 5,695,472 A | 12/1997 | Wyrick | |
| 5,957,897 A | 9/1999 | Jeffrey | |
| 6,099,504 A | 8/2000 | Gross et al. | |
| 6,149,626 A | 11/2000 | Bachynsky | |
| 6,306,420 B1 * | 10/2001 | Cheikh | 424/422 |
| 6,626,871 B1 * | 9/2003 | Smoliarov et al. | 604/263 |

FOREIGN PATENT DOCUMENTS

| | | |
|---|---|---|
| EP | 0982518 A2 | 3/2000 |
| HU | 194056 B | 1/1988 |
| HU | 197218 B | 3/1989 |
| WO | 94/13342 | 6/1994 |
| WO | 95/29720 | 11/1995 |
| WO | 95/31235 | 11/1995 |
| WO | WO 97/37705 | 10/1997 |
| WO | 98/00188 | 1/1998 |
| WO | 01/17593 | 3/2001 |

OTHER PUBLICATIONS

International Search Report PCT/US03/19988 dated Oct. 17, 2003.

Shape Memory Alloys, Online! Jun. 19, 2000, pp. 1-11, XP002255088. Retrieved from the Internet: <URL: web.archive.org/web/20001019173055/www.sma-inc.com/SMAPaper.html>'retrieved on Sep. 18, 2003! table 2.

International Search Report dated Oct. 17, 2003 for corresponding Appln. No. PCT/US03/19988.

* cited by examiner

REUSABLE, SPRING DRIVEN AUTOINJECTOR

This application claims the priority of provisional application Ser. No. 60/391,322, filed Jun. 24, 2002, which is incorporated herein by reference.

BACKGROUND

1. Field of the Invention

The present invention relates to reusable automatic injection devices. In particular, the present invention relates to automatic injection devices including a spring-loaded drive mechanism that incorporates one or more drive springs formed of a shape memory alloy.

2. State of the Art

Automatic injectors (hereinafter referred to as "autoinjectors") incorporating needled injection mechanisms are well known and are thought to exhibit several advantages relative to simple hypodermic syringes. For instance, because autoinjectors may be designed to automatically and reliably deliver a desired dose of medicament, they facilitate quick, convenient, and accurate delivery of medicaments. In particular, autoinjectors are well suited for use by subjects who must self-administer therapeutic substances or by healthcare workers who must inject multiple subjects over a relatively short period of time. Moreover, autoinjectors incorporating a needled injection mechanism may be designed so that the needle is hidden from view before, during, and even after an injection operation, thereby reducing or eliminating any anxiety associated with the act of penetrating a visible needle into the subject's tissue. Though their precise specifications vary widely, needled autoinjectors generally include a body or housing, a needled syringe or similar device, and one or more drive mechanisms for inserting a needle into the tissue of the subject and delivering a desired dose of liquid medicament through the inserted needle.

The drive mechanisms included in state of the art needled autoinjectors generally include a source of energy capable of powering the drive mechanism. This energy source may be, for example, mechanical (i.e., spring-loaded), pneumatic, electromechanical, or chemical, as described in U.S. Pat. Nos. 6,149,626, 6,099,504, 5,957,897, 5,695,472, 5,665, 071, 5,567160, 5,527,287, 5,354,286, 5,300,030, 5,102,393, 5,092,843, 4,894,054, 4,678,461, and 3,797,489, the contents of each such patent being incorporated herein by reference. International Publications numbered WO 01/17593, WO 98/00188, WO 95/29720, WO 95/31235, and WO 94/13342 also describe various injectors including different drive mechanisms. Nevertheless, needled autoinjectors more often incorporate drive mechanisms that utilize a coil spring as an energy source. Such spring-loaded drive mechanisms are desirable because they are thought to facilitate the creation of reliable autoinjectors that are relatively simple in design and inexpensive to manufacture.

In light of the growing desire to deliver increasingly viscous medicaments via a needled injection device, however, known spring-loaded drive mechanisms exhibit significant disadvantages. Specifically, the spring-loaded drive mechanisms included in state of the art needled autoinjectors are typically designed to generate forces sufficient for the injection of low viscosity medicaments, such as insulin and epinephrine, which generally exhibit viscosities near that of water (i.e., about 1 centipoise at 20° C.). Consequently, the spring-loaded drive mechanisms included in known autoinjectors are designed to exert only small injection forces (e.g., ranging from about 1 lb. to about 5 lbs.), which are not suitable for the delivery of emerging, injectable medicaments, such as bioerodible depot formulations, having viscosities much higher than that of water. As can be predicted using the Hagen-Poiseuille Law ($F=8Q\mu L(R^2/r^4)$), wherein "F" represents the injection force required, "Q" represents the flow rate of the material injected, "$\mu$" represents the viscosity of the material injected, "L" represents the length of the needle used, "R" represents the internal diameter of the reservoir containing the material to be injected, and "r" represents the internal diameter of the needle used, the injection forces required to deliver a dose of medicament through a needle of desirable gauge will easily exceed those typically provided by state of the art spring-loaded autoinjectors if the viscosity of the medicament to be delivered increases significantly beyond 1 centipoise.

A possible solution to the need for a spring-loaded drive mechanism capable of generating injection forces suitable for delivering higher viscosity medicaments would be to simply provide a drive mechanism including a heavier conventional spring capable of exerting a higher injection force. Yet, such an approach is not without difficulties. In particular, where the injector is designed as a multiple use device, the spring-loaded drive mechanism must be cocked such that the drive spring is held in a compressed position before each use, and in order to cock a conventional spring-loaded drive mechanism, a force that is equal to or greater than the maximum force exerted by the drive spring must be applied to the drive mechanism. It can be appreciated, then, that as the viscosity of the medicament to be delivered increases, not only does the injection force required to deliver the medicament increase, but the force required to cock the drive mechanism also increases. Where the material to be injected exhibits viscosities that approach those of proposed depot materials, the force required to cock a spring driven mechanism designed for delivery of the medicament could exceed that which could be reasonably applied by a user, even if the injector is provided with a cocking mechanism that provides some mechanical advantage that reduces the force that must be directly applied by the user to cock the drive mechanism.

It would be an improvement in the art, therefore, to provide a multiple use, spring-loaded autoinjector that includes a drive mechanism that can be cocked by a force that is lower than the injection force provided by the drive mechanism. Such an autoinjector could be designed to provide an injection force that is higher than the injection forces typically exerted by state of the art spring-loaded autoinjectors, while still allowing the user to cock the drive mechanism for reuse through the application of a force that is practically applicable.

SUMMARY OF THE INVENTION

The present invention provides a reusable, spring-driven autoinjector. The autoinjector of the present invention includes a body, a spring-loaded drive mechanism, a trigger mechanism, and a replaceable syringe cartridge. The body of the autoinjector of the present invention includes proximal and distal portions, with the proximal portion housing the drive mechanism and the distal portion housing the syringe cartridge. The drive mechanism includes one or more drive springs in association with a drive member, and the drive member is configured such that, upon compression of the one or more drive springs, the drive mechanism interacts with the trigger mechanism to place the drive mechanism in a cocked position within the proximal portion of the body of the autoinjector. The syringe cartridge provided in the autoinjector of the present invention includes a reservoir for containing the medicament to be delivered and a needle suitable for delivery of the medicament from the reservoir of the syringe cartridge and into the tissue of a subject. To prepare the autoinjector of the present invention for injection of a desired dose of medicament, the drive mechanism is placed in a cocked position and a syringe cartridge containing the medicament to be delivered is loaded into the proximal portion of the autoinjector body.

Once the drive mechanism is cocked and a syringe cartridge containing the desired medicament is loaded into the autoinjector of the present invention, the medicament contained in the syringe cartridge is injected into the subject by positioning the autoinjector at a desired injection site and actuating the trigger mechanism. Upon actuation of the trigger mechanism, the drive member is released from the cocked position, allowing the one or more springs included in the drive mechanism to expand from their compressed state. As the one or more drive springs expand from their compressed position, the drive member acts against the syringe cartridge in such a way that the needle of the syringe cartridge is inserted into the tissue of the subject and the medicament contained in the syringe cartridge is delivered through the needle at the injection site. After the medicament contained in the syringe cartridge has been delivered, the empty syringe cartridge may be removed from the distal portion of the body of the autoinjector and the drive mechanism can be re-cocked in preparation for another injection.

Advantageously, the one or more drive springs included in the drive mechanism of the autoinjector of the present invention are designed such that the drive mechanism can exert an injection force that is higher than the compressive force required to cock the drive mechanism. In order to achieve this capability, the one or more drive springs included in the autoinjector of the present invention are fabricated using a shape memory alloy (SMA). As used herein, the terms "shape memory alloy" and "SMA" include all alloys that exhibit two temperature dependent crystal structures or phases, with the lower temperature crystal phase being a "martensite" phase and the higher temperature crystal phase being an "austenite" phase. A drive spring made of an SMA is relatively stiff and capable of exerting a larger spring force when in an austenitic phase, but the same drive spring made of the same SMA becomes increasingly compliant and may be compressed through application of a relatively small force as the spring transitions into a martensite phase. Therefore, with the one or more drive springs in a martensite phase, the drive mechanism of the injector of the present invention can be cocked by the application of a relatively small compressive force, while transitioning the one or more drive springs into an austenite phase after the drive mechanism has been cocked allows the drive mechanism to exert a relatively large injection force upon triggering the injector. Through the use of one or more SMA drive springs, the injector of the present invention provides a reusable, spring-loaded autoinjector suitable for delivering medicaments requiring injection forces higher than those typically provided by state of the art autoinjectors, while simultaneously providing a device that can be cocked for re-use by the application of a compressive force that is practically applicable by a user.

The present invention also includes a method of injecting a medicament into a desired subject. The method of the present invention includes providing an autoinjector including a spring-loaded drive mechanism, using a first force to cock the spring-loaded drive mechanism, releasing the spring-loaded drive mechanism from the cocked position, and generating an injection force that is greater than the first force required to cock the spring-loaded drive mechanism and is sufficient to inject a desired dose of a medicament. The method of the present invention is easily varied, and specific embodiments of the method of the present invention may be tailored to suit virtually any desired operational context calling for the injection of a dose of medicament.

DETAILED DESCRIPTION OF THE INVENTION

Figure 1:
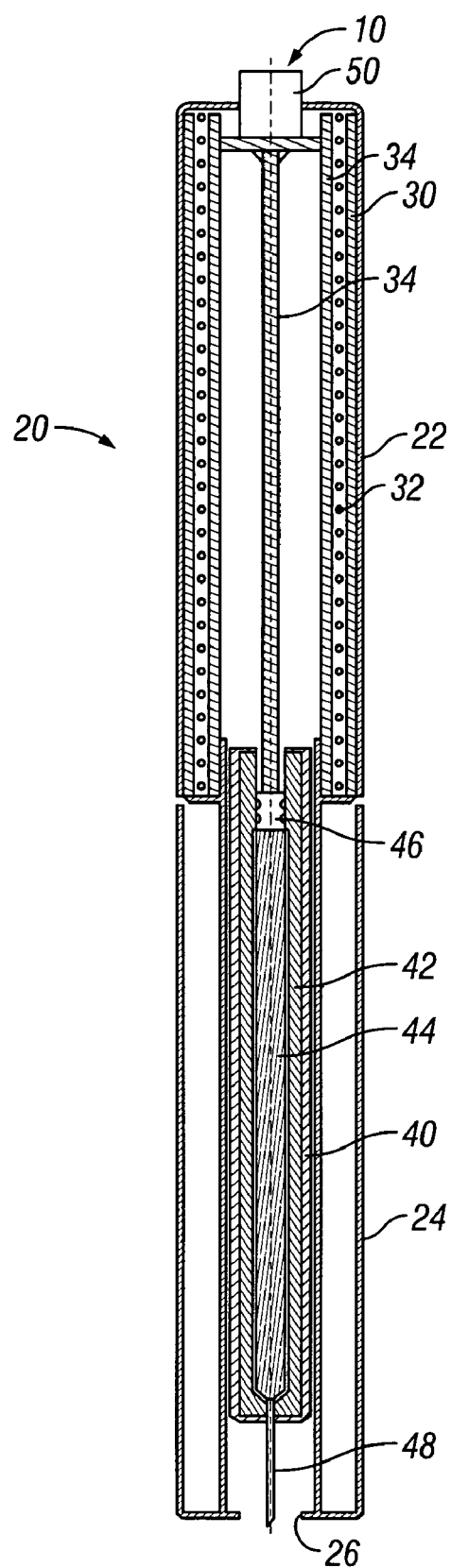
FIG. 1 provides a cross-sectional representation of an injection device according to the present invention.

A schematic representation of one embodiment of the injector 10 according to the present invention is provided in FIG. 1. As can be seen by reference to FIG. 1, the injector of the present invention includes a housing 20, a drive mechanism 30, a syringe cartridge 40, and a trigger mechanism 50. As can be appreciated in FIG. 1, the housing 20 of the injector 10 is divided into a proximal portion 22 and a distal portion 24. The proximal portion 22 serves to house the drive mechanism 30, which includes an SMA drive spring 32 and a drive member 34, while the distal portion 24 of the housing 20 houses a syringe cartridge 40 including a reservoir 42 suitable for containing a medicament 44, a piston 46 for expelling the medicament 44 from the reservoir 42, and a needle 48 through which the medicament 44 can be injected into a subject. This distal portion 24 of the housing 20 is configured such that the syringe cartridge 40 can be loaded into the distal portion 24 of the housing 20 in preparation for an injection and then removed after an injection has been completed. The trigger mechanism 50 of the injector 10 interacts with the drive member 34 of the drive mechanism 30 such that the drive member 34 is released from its cocked position upon actuation of the trigger mechanism 50.

As it is illustrated in FIG. 1, the drive mechanism 30 of the injector 10 is in its cocked position, with the drive member 34 maintained in a retracted position and the SMA drive spring 32 in a compressed state. Once the drive mechanism 30 is in its cocked position, the SMA drive spring 32 is transitioned into an austenitic state. With the drive mechanism 30 in a cocked position, the SMA drive spring 32 in an austenitic state, and a loaded syringe cartridge positioned in the distal portion 24 of the housing 20, an injection is initiated simply through actuation of the trigger mechanism 50. Actuation of the trigger mechanism 50 releases the drive member 34 from its cocked position, and upon release of the drive member 34, the SMA drive spring expands, motivating the drive member 34 axially with a desired injection force. In the embodiment illustrated in FIG. 1, as the drive member 34 is motivated by the SMA drive spring 32, the drive member 34 acts against the piston 46 of the syringe cartridge 40, causing the syringe cartridge 40 to move axially through the distal portion 24 of the housing 20 until the syringe cartridge 40 reaches a stop 26. Axial movement of the syringe cartridge 40 to the stop 26 causes the needle 48 associated with the syringe cartridge 40 to extend out from the distal portion 24 of the housing 20 and into a subject. The SMA drive spring 32 continues to expand even after the syringe cartridge 40 reaches the stop 26, which causes the drive member 34 to exert a continued injection force against the piston 46 of the syringe cartridge 34 and results in the expulsion of the medicament 44 from the reservoir 42 through the needle 48.

After the drive mechanism 30 of the injector 10 has been actuated and the medicament 44 contained in the syringe cartridge 40 has been expelled, the syringe cartridge 40 can be removed from the distal portion 24 of the housing 20 and the drive mechanism 30 can be re-cocked in preparation for a subsequent injection. In the embodiment shown in FIG. 1, the distal portion 24 of the housing 20 must be separated from the proximal portion 22 in order to either remove the syringe cartridge 40 or re-cock the drive mechanism 30. Before re-cocking the drive mechanism 30, the SMA drive spring 32 is transitioned back into a martensite phase. After the SMA drive spring 32 has been transitioned into a martensite phase, the drive mechanism 30 is manually re-cocked by simply applying a compressive force against the drive member 34 sufficient to compress the SMA drive spring 32 and force the drive member 34 back within the proximal portion 22 of the housing 20 such that drive member 34 is again retained in a cocked position by the trigger mechanism 50. Because the SMA drive spring 32 is transitioned to a martensite phase before the drive mechanism is re-cocked, the force required to compress the SMA drive spring 32 and re-cock the drive mechanism 30 is significantly reduced relative to the injection force exerted by the same SMA drive spring 32 in an austenitic state. After re-cocking the drive mechanism 30, the injector 10 is again made ready for an injection by loading an unused syringe cartridge 40 having a charge of medicament 44 into the distal portion 24 of the housing 20, reattaching the proximal portion 22 and distal portion 24 of the housing 20, and transitioning the SMA drive spring 32 into an austenitic state.

Though FIG. 1 provides a schematic representation of one embodiment of the injector of the present invention, the injector of the present invention is not limited to the representation provided in FIG. 1. Moreover, FIG. 1 provides only a general representation of each of the various components of the injector of the present invention for the purposes of illustration. Therefore, in each embodiment of the injector of the present invention, the components of the injector may vary, as desired, from the representation provided in FIG. 1, and each component of the injector may be embodied by any structure or mechanism suitable for providing a reusable injector including a drive mechanism that incorporates an SMA drive spring.

Though not represented in FIG. 1, the drive mechanism included in the injector of the present invention may also include more than one SMA drive spring. Providing the drive mechanism of the injector of the present invention with two or more SMA drive springs may be done in order to achieve an injection force that could not be practically achieved by a single spring. Where two or more SMA drive springs are used, the springs may be provided in a nested configuration, that is, with one or more smaller springs sized and wound to fit within the inner diameter of one or more larger springs. If two or more nested drive springs are provided in the drive mechanism of the injector of the present invention, the drive mechanism may be designed such that each drive spring is partitioned from the other drive spring(s) or is contained within its own sleeve or seat. However, two or more nested SMA drive springs may also be provided within the drive mechanism without partitioning. Where two or more nested SMA drive springs are nested without being partitioned one from another, each spring is preferably counter wound such that interference between the coils of the nested springs is prevented or minimized as the nested springs are repetitively compressed and released. Instead of two or more nested springs, the drive mechanism of the injector of the present invention may also include two or more SMA drive springs positioned in spaced apart relation to one another. For example, the drive member of the drive mechanism may be provided with two or more seats, with each seat positioned in a spaced apart relation to each of the other seats and each seat corresponding to one of the two or more SMA drive springs included in the drive mechanism. Regardless of whether the springs are nested or located in a spaced apart relationship one from another, however, where the drive mechanism of the injector of the present invention includes two or more SMA drive springs, the drive mechanism is configured such that the force generated by each of the SMA drive springs upon triggering the injector is exerted against the drive member included in the drive mechanism.

Instead of utilizing a simple coil spring (as is illustrated in FIG. 1), the drive mechanism of the injector of the present invention may also utilize a coiled wave spring formed of an SMA. Coiled wave springs are commercially available from, for example, Smalley® Steel Ring Company of Lake Zurich, Ill., U.S.A. As the name suggests, the material forming a coiled wave spring is not only coiled but waved, and due to such a structure, coiled wave springs can reduce the spring height necessary to achieve a desired spring force at a given spring rate over a given stroke by as much as 50%. Therefore, the use of an SMA coiled wave spring as the drive spring in the drive mechanism of the injector of the present invention may facilitate the fabrication of an injector that is relatively shorter in length when compared to an injector powered by a simple SMA coil spring designed to provide a comparable spring force at a given rate over a given stroke.

The one or more SMA drive springs included in the drive mechanism of the injector of the present invention are not only variable in number and configuration, but the formulation of the SMA used to fabricate the one or more drive springs can also be varied to achieve desired performance characteristics. Though any SMA suitable for use in an injector may be used to fabricate the one or more drive springs incorporated in the drive mechanism of the injector of the present invention, SMA alloys that are presently preferred include NiTi, CuZnAl, NiTiCu, and CuAlNi alloys. Advantageously, SMA compositions, such as the preferred alloys noted herein, are easily varied to create drive springs exhibiting force and rate characteristics that provide a desired range of spring forces over a stroke that ensures both insertion of the needle associated with the syringe cartridge and delivery of a desired dose of medicament.

The alloy compositions used to fabricate the one or more SMA drive springs included in the injector of the present invention may also be varied to control the temperatures at which the springs enter their martensite or austenite phases. Generally, upon heating and cooling, SMA compositions do not undergo a complete phase transformation at a single, specific temperature. Instead, the transformation from one crystal phase to another begins at one temperature (i.e., the martensite start ($M_s$) temperature or the austenite start ($A_s$) temperature) and is completed at a second temperature (i.e., the martensite finish ($M_f$) temperature or the austenite finish ($A_f$) temperature), with the difference between the temperature at which the SMA is about 50% transformed in the austenite phase ($A_p$) and the temperature at which the SMA is about 50% transformed in the martensite phase ($M_p$) defining the hysteresis width of the SMA. By altering the relative percentages of the metals included in an SMA or by including additional metals, such as, for example, iron or chromium, in an SMA composition, the drive springs included in the drive mechanism of the injector of the present invention can be formulated to exhibit a desired hysteresis width with martensite and austenite transition points within one or two degrees of a pre-defined set of $M_s$, $M_f$, $A_s$, and $A_f$ temperatures. Beyond adjustments to the alloy composition, the martensite and austenite transition temperatures or hysteresis width for a given SMA can also be adjusted through known annealing processes.

The variability of SMA compositions allows the injector of the present invention to be tailored for use in virtually any desired range of operational temperatures. As it is used herein the phrases "range of operational temperatures" and "operational temperature range" indicate the temperature range required to achieve the desired austenite and martensite phase transitions in the one or more SMA drive springs included in the drive mechanism. Though the operational temperature range of the injector of the present invention will typically extend above or below the anticipated ambient temperature range of the environment of use in order to achieve desired martensite and austenite transitions, the anticipated ambient temperature range for the anticipated environment of use will fall within the operational temperature range of the injector. In one embodiment, the SMA used to create the one or more drive springs included in the drive mechanism of the injector of the present invention is formulated such that the one or more drive springs are in a desired austenite phase within the anticipated ambient temperature range but require cooling in order to achieve a desired martensite phase. In an alternative embodiment, the SMA used to create the one or more drive springs is formulated such that the one or more drive springs are in a desired martensite phase within the anticipated ambient temperature range, but require heating in order to achieve a desired austenite phase. In yet a further embodiment, the SMA used to create the one or more drive springs is formulated such that heating above the anticipated ambient temperature range is required to achieve a desired austenite phase and cooling below the anticipated ambient temperature range is required to achieve a desired martensite phase.

Health care facility and home environments are exemplary environments of use for the injector of the present invention. In such environments, the operational temperature ranges of injectors according to the present invention will preferably fall between temperatures typical for refrigerated storage (about 4° C.) and temperatures approximating human body temperature (about 37° C.). Of course, where desired, the operational temperature range for an injector designed for use in a health care facility or home environment may extend above or below such a temperature range. The ambient temperature range in a health care facility or home environment may be taken generally as room temperature (between about 20° C. and about 25° C.). Therefore, where the injector of the present invention is designed for use in a health care facility or home, the injector preferably incorporates one or more SMA drive springs that achieve a desired martensite phase at or above about 4° C., while achieving a desired austenite phase at or below about 37° C. More preferably, to ease the use of an injector according to the present invention designed for health care facility or home use, the SMA used to create the one or more drive springs of the injector preferably provides an operational temperature range that either extends below or above an ambient temperature between about 20° C. and about 25° C. but does not extend both above and below such an ambient temperature range. For example, in a presently preferred embodiment, the injector includes one or more SMA drive springs that transition to a desired austenite phase between about 20° C. and about 25° C., while transitioning to a desired martensite phase at or above about 4° C. In another presently preferred embodiment, the injector of the present invention includes one or more SMA drive springs that transition to a desired austenite phase at about 37° C., while transitioning to a desired martensite phase between about 20° C. and about 25° C. Of course, the injector of the present invention is not limited to injectors designed for health care facility or home use, and the one or more drive springs included in the drive mechanism of the injector of the present invention may be fabricated of an SMA formulated to perform in an operational temperature range that is suitable for virtually any desired environment of use.

Where the temperature required to achieve a desired austenitic phase is higher than the anticipated ambient temperature of the environment of use (e.g., room temperature), the injector of the present invention may be provided a heating mechanism. Such a mechanism may be internal to or external to the housing of the injector. Where the heating mechanism is internal to the housing of the injector, the internal heating mechanism may be embodied by any suitable radiant heat or electrical energy source. For example, an internal heating mechanism may incorporate a heating mechanism that utilizes one or more batteries to transfer electrical energy to the one or more SMA drive springs, which, in turn, increases the temperature of the one or more SMA drive springs and allows a desired austenite phase to be achieved. Where the heating mechanism is external from the housing of the injector, any known external heating technology may be used to warm the one or more drive springs to a desired austenite phase.

Though shape memory alloys may be formulated to provide a superelastic mode of operation, wherein the transformation between the martensite and austenite states occurs through the application of a stress or other force load, the SMA used to fabricate the one or more drive springs included in the drive mechanism of the injector of the present invention is preferably formulated and processed to provide a shape memory mode of behavior within the anticipated operational temperature range. In order to achieve an SMA drive spring that operates in a shape memory mode, the SMA composition used to create the one or more SMA drive springs included in the injector preferably exhibits $A_f$ and $M_f$ temperatures within the anticipated operational temperature range of the injector. Such a composition advantageously ensures that the one or more SMA drive springs included in the injector of the present invention are fully martensitic in the lower end of the injector's operational temperature range and fully austenitic at the upper end of the injector's operational temperature range.

However, achieving a shape memory mode of behavior does not necessitate that the one or more drive springs transition to either a fully austenite phase or a fully martensite phase within the anticipated operational temperature range. The SMA composition used to form the one or more drive springs need only exhibit enough shape memory behavior to provide a crystal phase transition within the operational temperature range that is sufficient to reduce the force required to compress the one or more SMA drive springs as they cool from the upper end of the operational temperature range to the lower end of the operational temperature range. Regardless of whether the SMA composition is fully martensitic or fully austenitic within injector's operational temperature range, the SMA composition used to form the one or more drive springs of the injector of the present invention preferably provides a drive spring that exhibits at least a 20% reduction in the force required to compress the drive spring as the drive spring transitions from an austenite phase at the upper end of the operational temperature range to a martensite phase at the lower end of its operational temperature range. More preferably, the SMA material used to form the one or more drive springs provides a drive spring exhibiting at least a 30% reduction in the force required to compress the drive spring as the drive spring is transitioned from an austenite phase to a martensite phase at the upper and lower ends of its operational temperature range, respectively. Even more preferably, the SMA material used to form the one or more drive springs provides a drive spring exhibiting at least a 40% reduction in the force required to compress the drive spring as the drive spring is transitioned from an austenite phase to a martensite phase at the upper and lower ends of its operational temperature range, respectively. Most preferably, the SMA material used to form the one or more drive springs provides a drive spring exhibiting at least a 50% reduction in the force required to compress the drive spring as the drive spring is transitioned from an austenite phase to a martensite phase at the upper and lower ends of its operational temperature range, respectively.

Figure 2:
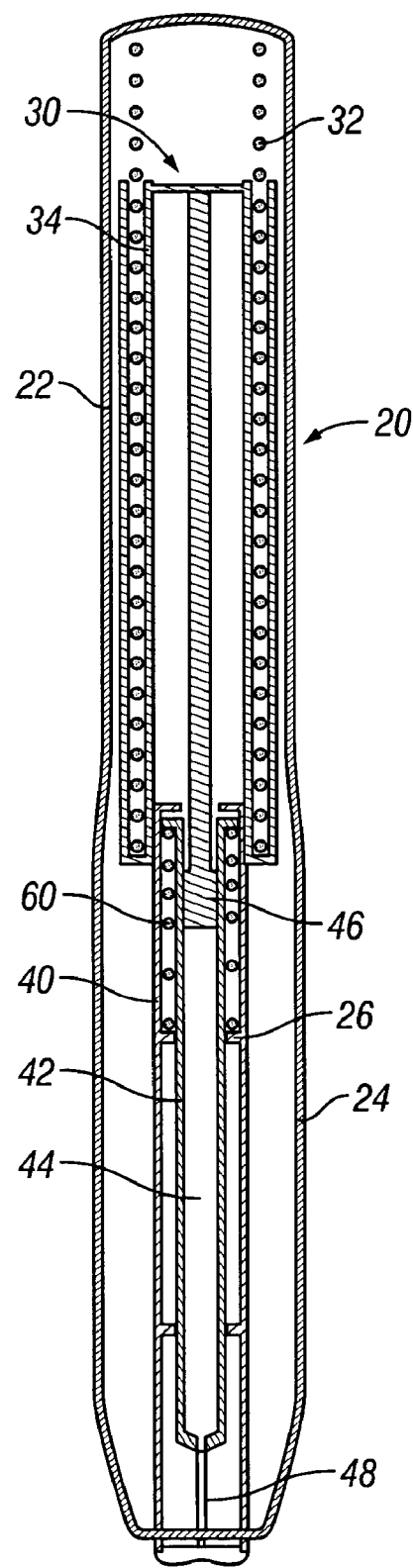
FIG. 2 provides a cross-sectional representation of a second injection device according to the present invention.

However, the composition, structure, and number of the one or more SMA drive springs included in the injector of the present invention are not the only components of the injector that may be varied to achieve an injector exhibiting desired performance characteristics. The representation provided in FIG. 1 is meant only to facilitate an understanding of the injector of the present invention and does not limit the specific configuration of any of the components of the injector 10 of the present invention. For example, as shown in FIG. 2, a schematic representation of a second embodiment of the injector 10 of the present invention, the distal portion 24 of the housing 20 may include a bias spring 60 positioned to bias the syringe cartridge 40 in a retracted position within the distal portion 24 of the housing and to dampen the injection force sensed by the user or the subject. As can be seen in FIG. 2, where a bias spring 60 is included in the distal portion 24 of the housing 20, it is preferably positioned to act against the reservoir 42 of the syringe cartridge 40, not directly against the drive mechanism 30. Such a configuration allows the dampening of the spring force sensed by the user or subject, without actually reducing the injection force that is exerted by the drive mechanism 30 against the medicament 44 to be delivered.

Each of the components included in the injector of the present invention may be configured as desired to achieve an injector providing one or more targeted performance characteristics. Various structures for two-part injector housings, triggering mechanisms, and syringe cartridges are known in the art and may be used as desired in fabricating an injector according to the present invention. Patent publications teaching such structures include, for example, U.S. Pat. Nos. 6,149,626, 5,957,897, 5,695,472, 5,665,071, 5,354,286, 5,300,030, 5,102,393, 5,092,843, 4,678,461, and 3,797,489, the contents of each of which are incorporated herein by this reference. However, the injector of the present invention is not limited to the housings, triggering mechanisms, and syringe cartridges taught in these patents. The injector of the present invention may include any structure or mechanism for providing a housing, triggering mechanism, or syringe cartridge that is suitable for use in a reusable injector including a drive mechanism that incorporates one or more SMA drive springs. Moreover, the injector of the present invention may include features not encompassed by the schematic illustrations provided in FIG. 1 and FIG. 2. For example, the injector of the present invention may incorporate one or more needle safe mechanisms, such as a drive mechanism that provides automatic retraction of the needle within the distal portion of the housing upon completion of an injection or a spring-loaded sleeve positioned on the distal portion of the housing, the spring-loaded sleeve designed to automatically extend over a needle extending from the distal portion of the housing upon removal of the injector from the injection site.

Though the injector of the present invention may be embodied by injectors of varying specifications, each embodiment of the injector according to the present invention includes one or more SMA drive springs that provide a drive mechanism that exerts an injection force that is greater than the compressive force required to cock the drive mechanism. The injector of the present invention therefore facilitates the creation of relatively simple autoinjection mechanisms capable of exerting injection forces higher than the injection forces typically achieved by state of the art spring-loaded autoinjectors, while providing a drive mechanism that can be practically cocked by the user. However, as described herein, the one or more SMA drive springs included in the injector of the present invention may be fabricated to exert a wide range of injection forces. Thus, the injector of the present invention is not limited to an injector exerting an injection force that is greater than the injection forces typically exerted by state of the art injectors. If desired, the injector of the present invention may in fact be configured to exert an injection force that is equal to or even below the injection forces typically exerted by state of the art spring driven autoinjectors. Such an injector would still achieve the benefit of exerting an injection force that is higher than the force required to cock the drive mechanism and thereby serve to increase the ease with which a user can use and re-use the injector.

The present invention also includes a method of injecting a medicament into a desired subject. In general, the method of the present invention includes providing an autoinjector including a spring-loaded drive mechanism, using a first force to cock the spring-loaded drive mechanism, releasing the spring-loaded drive mechanism from the cocked position, and generating an injection force that is greater than the first force required to cock the spring-loaded drive mechanism and is sufficient to inject a desired dose of a medicament. In a specific embodiment, the method of the present invention further includes providing an autoinjector including a spring-loaded drive mechanism incorporating one or more drive springs formed of an SMA, placing the one or more drive springs in a martensite phase before cocking the drive mechanism, and placing the one or more drive springs in an austenitic phase after the drive mechanism is cocked but before the spring-loaded drive mechanism is released from the cocked position. Of course, the method of the present invention is as variable as the injector of the present invention and, as is easily appreciated, the method of the present invention may be tailored to suit various delivery contexts just as the various components of the injector of the present invention may be varied to achieve targeted performance characteristics.

We claim:

1. An autoinjector comprising:
    a housing;
    a reservoir for containing a medicament in a distal portion of the housing;

a needle for delivering the medicament;

a drive mechanism in a proximal portion of the housing, the drive mechanism being capable of exerting a force sufficient to expel the medicament from the reservoir through the needle, the drive mechanism comprising a shape memory alloy drive spring, the shape memory alloy drive spring being formulated to exert a first force when in a martensite phase and a second force, which is larger than the first force, when in an austenite phase, the drive mechanism being capable of being manually re-cocked when the shape memory alloy drive spring is in the martensite phase.

2. The autoinjector of claim 1, wherein the first force is at least 20% less than the second force.

3. The autoinjector of claim 1, wherein the first force is at least 30% less than the second force.

4. The autoinjector of claim 1, wherein the first force is at least 40% less than the second force.

5. The autoinjector of claim 1, wherein the first force is at least 50% less than the second force.

6. The autoinjector of claim 1, wherein the shape memory alloy drive spring is formulated to provide a shape memory mode of behavior within an operational temperature range of the autoinjector.

7. The autoinjector of claim 1, wherein the shape memory alloy drive spring is fabricated of a shape memory alloy that is in an austenite phase within an ambient temperature range of an environment of use of the autoinjector.

8. The autoinjector of claim 7, wherein the ambient temperature range of the environment of use is about 20° C. to about 25° C.

9. The autoinjector of claim 8, wherein the shape memory alloy drive spring is fabricated using a shape memory alloy that is in a martensite phase at a temperature that is at or above about 4° C.

10. The autoinjector of claim 1, wherein the shape memory alloy drive spring is fabricated of a shape memory alloy that is in a martensite phase within an ambient temperature range of an environment of use of the autoinjector.

11. The autoinjector of claim 10, wherein the ambient temperature range of the environment of use is about 20° C. to about 25° C.

12. The autoinjector of claim 11, wherein the shape memory alloy drive spring is fabricated using a shape memory alloy that is in an austenite phase at or above about 37° C.

13. The autoinjector of claim 1, wherein the shape memory alloy drive spring is formed of a shape memory alloy formulated to achieve a full austenite phase and a full martensite phase within an operational temperature range of the autoinjector.

14. The autoinjector of claim 13, wherein the operational temperature range of the autoinjector is from about 4° C. to about 37° C.

15. The autoinjector of claim 1, wherein the shape memory alloy drive is a coiled wave spring.

* * * * *